US00PP11811P2

(12) United States Plant Patent
van Rijn

(10) Patent No.: US PP11,811 P2
(45) Date of Patent: Mar. 13, 2001

(54) ANTHURIUM PLANT NAMED 'HAPPY LOVE'

(75) Inventor: Leonardus van Rijn, Schipluiden (NL)

(73) Assignee: Rijnplant, Schipluiden (NL)

( * ) Notice: Subject to any disclaimer, the term of this patent is extended or adjusted under 35 U.S.C. 154(b) by 0 days.

(21) Appl. No.: 09/291,092

(22) Filed: Apr. 14, 1999

(51) Int. Cl.[7] ..... A01H 5/00
(52) U.S. Cl. ..... Plt./365

(58) Field of Search ..... Plt./365, 369

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Anthurium plant named 'Happy Love', characterized by its upright plant habit; freely clumping growth habit; durable dark green leaves that are ovate to lanceolate in shape; numerous inflorescences that are positioned upright and beyond the foliage on strong and erect scapes; durable, glossy orange red spathes; year-round continuous flowering; and good post-production longevity.

1 Drawing Sheet

BACKGROUND OF THE INVENTION

The present invention relates to a new and distinct cultivar of Anthurium plant, botanically known as *Anthurium andreanum*, and hereinafter referred to by the cultivar name 'Happy Love'.

The new Anthurium is a product of a planned breeding program conducted by the Inventor in Schipluiden, The Netherlands. The objective of the program is to create and develop new Anthurium cultivars that have a freely clumping growth habit, strong and vigorous plant growth, attractive spathe color, numerous inflorescences and leaves, and good post-production longevity.

The new Anthurium originated from a cross by the Inventor on Apr. 25, 1994 of the Inventor's proprietary *Anthurium andreanum* selection code No. 92-3 as the female, or seed, parent with the Inventor's proprietary *Anthurium andreanum* selection code No. 93-22 as the male, or pollen, parent. The cultivar 'Happy Love' was discovered and selected by the Inventor as a plant within the progeny of the stated cross in a controlled environment in Schipluiden, The Netherlands in April, 1996.

Asexual propagation of the new cultivar by tissue culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar 'Happy Love'. These characteristics in combination distinguish 'Happy Love' as a new and distinct cultivar:

1. Upright plant habit.

2. Freely clumping growth habit.

3. Durable dark green leaves that are ovate to lanceolate in shape.

4. Numerous inflorescences that are positioned upright and beyond the foliage on strong and erect scapes.

5. Durable, glossy orange red spathes.

6. Year-round continuous flowering.

7. Good post-production longevity.

The new Anthurium can be compared to the female parent, the Inventor's proprietary selection code No. 92-3. In side-by-side comparisons conducted by the Inventor in Schipluiden, The Netherlands, plants of the new Anthurium differ from plants of selection code No. 92-3 in the following characteristics:

1. Plants of the new Anthurium are more compact than plants of the selection code No. 92-3.

2. Plants of the new Anthurium have smaller leaves than plants of the selection code No. 92-3.

3. Plants of the new Anthurium have smaller spathes than plants of the selection code No. 92-3.

4. Spathe color of the new Anthurium is more orange than spathe color of the selection code No. 92-3.

The new Anthurium can be compared to the male parent, the Inventor's proprietary selection code No. 93-22. In side-by-side comparisons conducted by the Inventor in Schipluiden, The Netherlands, plants of the new Anthurium differ from plants of selection code No. 93-22 in the following characteristics:

1. Plants of the new Anthurium grow faster than plants of the selection code No. 93-22.

2. Plants of the new Anthurium have smaller leaves than plants of the selection code No. 93-22.

3. Spathe color of the new Anthurium is more orange than spathe color of the selection code No. 93-22.

4. Plants of the new Anthurium and plants of the selection code No. 93-22 differ in spathe shape.

The new Anthurium can be compared to the Anthurium cultivar 'Champion', disclosed in U.S. Plant Pat. No. 9,088. In side-by-side comparisons conducted by the Inventor in Schipluiden, The Netherlands, plants of the new Anthurium differ from plants of the cultivar 'Champion' in the following characteristics:

1. Plants of the new Anthurium grow faster than plants of the cultivar 'Champion'.

2. Plants of the new Anthurium are more freely clumping than plants of the cultivar 'Champion'.

3. Plants of the new Anthurium have larger leaves than plants of the cultivar 'Champion'.

4. Spathes of the new Anthurium are not as round and are more orange in color than spathes of the cultivar 'Champion'.

BRIEF DESCRIPTION OF THE PHOTOGRAPH

The accompanying colored photograph illustrates the overall appearance of the new Anthurium, showing the colors as true as it is reasonably possible to obtain in colored reproductions of this type. The photograph comprises a top perspective view of a typical potted plant of the cultivar 'Happy Love'. Leaf, spathe and spadix colors in the photograph may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe one-year old plants grown in 14-cm pots in Schipluiden, The Netherlands, in a glass greenhouse with an average day temperature of 25° C. and an average night temperature of 19° C.

Botanical classification: *Anthurium andreanum* cultivar 'Happy Love'.

Parentage:

*Female parent.*—Inventor's proprietary *Anthurium andreanum* selection code No. 92-3.

*Male parent.*—Inventor's proprietary *Anthurium andreanum* selection code No. 93-22.

Propagation:

*Method.*—By tissue culture.

*Time to develop roots.*—About 70 or 84 days at 24° C. or 21° C., respectively are required to root a tissue-cultured plantlet.

*Rooting habit.*—Numerous and very strong fleshy roots.

Plant description:

*Plant shape.*—Upright, inverted triangle, symmetrical.

*Growth habit.*—Freely clumping, bushy and dense, about four to six shoots per plant. Appropriate for 12 to 20-cm containers.

*Plant height.*—About 35 to 40 cm from soil level to leaf plane and about 40 and 50 cm from soil level to apex of spathes.

*Plant width.*—About 40 to 50 cm.

*Plant vigor.*—High.

*Growth rate.*—Rapid.

*Crop time.*—About 6 and 12 months are usually required from planting of young plants to finished plants in 12 and 20-cm containers, respectively.

*Foliage description.*—Quantity: Usually about four to seven per shoot; about 16 to 42 leaves per container. Length: About 14 to 20 cm. Width: About 7 to 13 cm. Shape: Ovate to lanceolate. Apex: Apiculate. Base: Strongly auriculate; lobes not overlapping. Margin: Entire. Texture: Smooth, glabrous, leathery. Color: Young leaves, upper surface: 137A to 147A. Young leaves, lower surface: 138B to 137D. Mature leaves, upper surface: Darker than 137A. Mature leaves, lower surface: Darker than 146C to 144B. Petiole: Length: About 20 to 28 cm. Color: Close to 146B. Geniculum length: About 1.5 to 2 cm; slightly longer on older peduncles. Geniculum diameter: About 3 to 5 mm. Geniculum color: 144B; older leaves with purple anthocyanin.

Inflorescence description:

*Inflorescence arrangement.*—Spathes with spadices held beyond the foliage. Flowering structures arise from leaf axils. Freely flowering; continuous flowering year-round; numerous spathes/spadices per plant.

*Inflorescence longevity.*—Spathes/spadices last about six weeks under winter conditions and about three months under summer conditions; persistent.

*Flowers.*—Quantity per spadix: Numerous, about 200. Shape: Rounded. Diameter: About 1 mm, maximum.

*Spathe.*—Length: About 8 to 11 cm. Width: About 8 to 10 cm. Shape: Broadly cordate. Apex: Apiculate to cuspidate. Base: Auriculate; lobes not overlapping. Margin: Entire. Texture: Leathery, glabrous, moderate blistering, glossy. Color: When opening: 40A to 43A. Front surface: 40A to 43A. Back surface: 41B to 41C. After senescence: 44C; lobes edged with green, 144B; area of green increases with development.

*Spadix.*—Length: About 6 to 8 cm. Diameter: Midsection, about 8 mm; apex, about 5 mm. Shape: Columnar. Cross section: Rounded. Longitudinal axis: Weakly recurved, about 45° to spathe. Color: Base and mid-section: 159D. Apex: 24A. After senescence: 146A.

*Scape.*—Length: About 30 to 40 cm. Aspect: Strong and erect. Color: Base, 146B; slight purple anthocyanin towards apex.

*Reproductive organs.*—Androecium: Pollen color: Creamy white, 158D. Gynoecium: Stigma shape: Ovoid. Ovary: Protogyneous.

Disease resistance: Plants of the new Anthurium have exhibited good resistance to root diseases common to Anthurium.

Seed development: Seed development on plants of the new Anthurium has not been observed.

It is claimed:

1. A new and distinct cultivar of Anthurium plant named 'Happy Love', as illustrated and described.

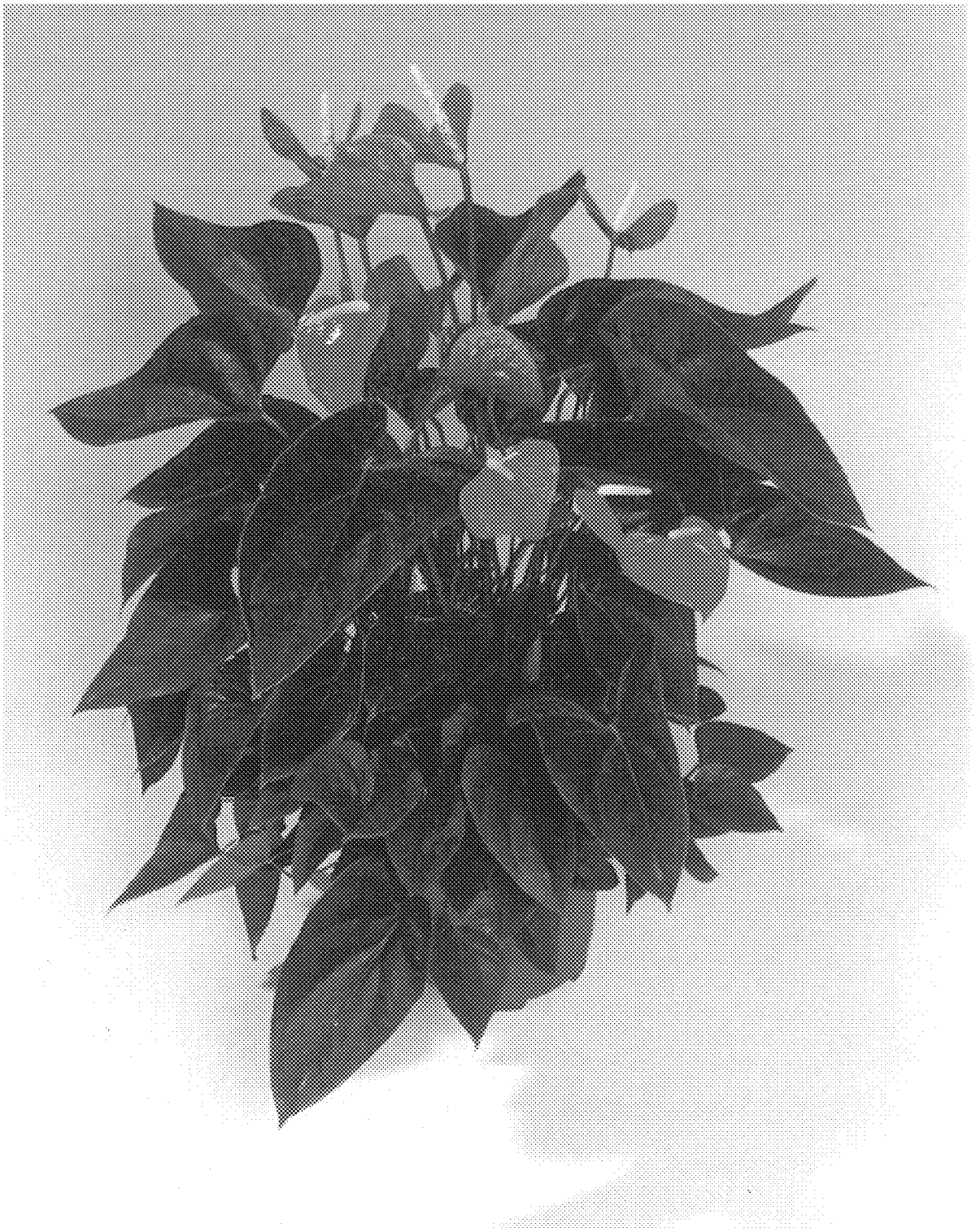

* * * * *